United States Patent [19]

Takahata et al.

[11] Patent Number: 5,191,131
[45] Date of Patent: Mar. 2, 1993

[54] PROCESS FOR PREPARATION OF LOWER ALIPHATIC HYDROCARBONS

[75] Inventors: Kazunori Takahata; Toshihiro Murashige, both of Waki; Yukimasa Shigemura, Ichihara; Hiroshi Takaki, Ichihara; Akihiko Okano, Ichihara, all of Japan

[73] Assignee: Research Association for Utilization of Light Oil, Tokyo, Japan

[21] Appl. No.: 444,980

[22] Filed: Dec. 4, 1989

[30] Foreign Application Priority Data

Dec. 5, 1988 [JP] Japan ................................. 63-307270
Dec. 5, 1988 [JP] Japan ................................. 63-307271
Mar. 3, 1989 [JP] Japan ................................. 1-51546
May 29, 1989 [JP] Japan ................................. 1-135364

[51] Int. Cl.$^5$ ........................... C07C 4/06; C07C 5/333
[52] U.S. Cl. .................................... 585/324; 585/648; 585/649; 585/651; 585/653; 585/661; 585/662
[58] Field of Search ............... 585/324, 648, 649, 654, 585/661, 662, 752, 651, 650, 653

[56] References Cited

U.S. PATENT DOCUMENTS

| | | | |
|---|---|---|---|
| 3,598,724 | 8/1971 | Mulasky | 585/752 |
| 3,923,641 | 12/1975 | Morrison | 585/752 |
| 4,085,156 | 4/1978 | Frilette et al. | 585/653 |
| 4,157,950 | 6/1979 | Frilette et al. | 585/752 |
| 4,162,214 | 7/1979 | Maslyansky | 585/752 |
| 4,172,813 | 10/1979 | Feinstein et al. | 585/475 |
| 4,542,248 | 9/1985 | Lucien | 585/661 |
| 4,560,824 | 12/1985 | Spence et al. | 585/662 |
| 4,565,898 | 1/1986 | O'Hara et al. | 585/661 |
| 4,764,266 | 8/1988 | Chen et al. | 585/739 |
| 4,806,624 | 2/1989 | Herber et al. | 585/662 |

Primary Examiner—Anthony McFarlane
Attorney, Agent, or Firm—Sherman and Shalloway

[57] ABSTRACT

A paraffin having 5 to 10 carbon atoms is catalytically cracked in the presence of a catalytically cracking catalyst having a strong acidity, especially a rare earth metal ion-exchanged mordenite or a dealuminized mordenite, to form a paraffin having 3 or 4 carbon atoms. The formed paraffin is contacted with a dehydrogenation catalyst to obtain an olefin having 3 or 4 carbon atoms.

15 Claims, 1 Drawing Sheet

PROCESS FOR PREPARATION OF LOWER ALIPHATIC HYDROCARBONS

BACKGROUND OF THE INVENTION (1) Field of the Invention

The present invention relates to a process for preparing a lower aliphatic hydrocarbon comprising an olefin having 3 or 4 carbon atoms as a main component from a hydrocarbon having 5 to 10 carbon atoms. Furthermore, the present invention relates to a process for preparing a lower hydrocarbon comprising a paraffin having 3 or 4 carbon atoms as a main component by the catalytic cracking by using a specific mordenite catalyst.

(2) Description of the Prior Art

Various investigations have been made from old on the trial to obtain a fraction having 3 or 4 carbon atoms, which is industrially valuable, in a high yield from a petroleum type hydrocarbon compound, represented by naphtha or the like, as the starting material. However, only the thermal cracking is adopted as the industrial process, and the operation is carried out under such conditions that the yield of a fraction having 2 or 3 carbon atoms is highest. As the known process comprising catalytically cracking a hydrocarbon to prepare a paraffin and/or olefin having a reduced carbon number, a process using a silica/alumina type oxide or zeolite as the catalyst is disclosed in "Petroleum Refining Process", page 59 (1978), compiled by the Association of Petroleum and Industrial & Engineering Chemistry, 39, (8), 1032 (1947). However, this process is defective in that a high temperature of 500° to 600° C. or a higher temperature is necessary and hence, the amount formed of a hydrocarbon having 1 or 2 carbon atoms is large and the selectivity to a hydrocarbon having 3 or 4 carbon atoms, intended in the present invention, is low, and that reduction of the activity of the catalyst is violent. In Journal of Catalysis, 6, 278 (1966), it is taught that a hydrogen ion-exchanged mordenite type zeolite exerts an effect for the cracking reaction to a hydrocarbon having 3 to 4 carbon atoms. However, this catalyst is not satisfactory in the selectivity to a hydrocarbon having 3 or 4 carbon atoms and the yield, and the performances are insufficient as the industrial catalyst.

Furthermore, there is proposed a process in which an olefin having 3 or 4 carbon atoms is prepared by dehydrogenating a paraffin having 3 or 4 carbon atoms. For example, there can be mentioned a process in which propylene is prepared by dehydrogenating propane at a temperature of 570° to 680° C. in the presence of a chromium/aluminum type catalyst (U.S. Pat. No. 3,665,049) and a process in which propylene is prepared by dehydrogenating propane at 300° to 700° C. in the presence of a catalyst comprising platinum and magnesium oxide or manganese oxide supported on a zeolite (Japanese Unexamined Patent Publication No. 61-197040). These processes, however, are defective in that the amount formed of a hydrocarbon having 1 or 2 carbon atoms is large and the yield of the intended olefin is low.

In Japanese Unexamined Patent Publication No. 62-22891 proposed by us, there is disclosed a process in which a paraffin and/or olefin having 3 or 4 carbon atoms is prepared by the catalytic cracking of a paraffin having 5 to 10 carbon atoms in the presence of a catalyst formed by treating a metal oxide or composite metal oxide with a fluorine-containing compound. According to this process, the paraffin and olefin are prepared in the form of a mixture, and it is difficult to form the olefin at a high selectivity.

SUMMARY OF THE INVENTION

It is a primary object of the present invention to provide a process for preparing an olefin having 3 or 4 carbon atoms at a high selectivity and in a high yield from a paraffin having 5 to 10 carbon atoms or a hydrocarbon comprising this paraffin as the main component.

Another object of the present invention is to provide a process for preparing an olefin having 3 or 4 carbon atoms from a paraffin having 5 to 10 carbon atoms while controlling formation of a hydrocarbon having 1 or 2 carbon atoms.

Still another object of the present invention is to provide a process for preparing a paraffin having 3 or 4 carbon atoms from a paraffin having 5 to 10 carbon atoms at a high selectivity and in a high yield.

A further object of the present invention is to provide a process for the catalytic cracking of a paraffin having 5 to 10 carbon atoms, in which the activity of the catalyst can be maintained at a high level stably for a long time and an intended paraffin having 3 or 4 carbon atoms can be continuously prepared at a high selectivity and in a high yield.

In accordance with one aspect of the present invention, there is provided a process for the preparation of a lower aliphatic hydrocarbon comprising an olefin having 3 or 4 carbon as the main component from a paraffin having 5 to 10 carbon atoms or a hydrocarbon comprising this paraffin as the main component, which comprises carrying out the first reaction of catalytically cracking a paraffin having 5 to 10 carbon atoms or a hydrocarbon comprising this paraffin as the main component in the presence of a catalytic cracking catalyst having a strong acidity, especially a rare earth metal ion-exchanged mordenite catalyst or a dealuminized mordenite catalyst to convert the paraffin or hydrocarbon, to a hydrocarbon comprising a paraffin having 3 to 4 carbon atoms as the main component, and carrying out the second reaction of dehydrogenating the hydrocarbon comprising a paraffin having 3 to 4 carbon atoms as the main component, obtained at the first reaction, with a dehydrogenation catalyst to convert the hydrocarbon to a lower aliphatic hydrocarbon comprising an olefin having 3 to 4 carbon atoms as the main component.

In accordance with another aspect of present invention, there is provided a process for the preparation of a lower aliphatic hydrocarbon, which comprises catalytically cracking a paraffin having 5 to 10 carbon atoms or a hydrocarbon comprising said paraffin as the main component to form a lower a aliphatic hydrocarbon comprising a paraffin having 3 to 4 carbon atoms as the main component, a mordenite catalyst ion-exchanged with a rare earth metal component or a mordenite catalyst dealuminized by an acid treatment is used as the catalyst.

In accordance with still another aspect of the present invention, there is provided a process for the preparation of a lower aliphatic hydrocarbon comprising a paraffin having 3 to 4 carbon as the main component, which comprises bringing a paraffin having 5 to 10 carbon atoms or a hydrocarbon comprising said paraffin as the main component with a catalyst composed of a mordenite at a temperature of 300° to 550° C. in a fluidized bed to form a cracking reaction product comprising a paraffin having 3 to 4 carbon atoms as the main component, withdrawing a part of the catalyst together with the cracking product from the reaction system, separating the cracking product from the cracking reaction product, regenerating the separated catalyst by a burning treatment at a temperature of 400° to 800° C., and circulating the regenerated catalyst to the reaction system.

DETAILED DESCRIPTION OF THE PREFERRED EMBODIMENTS

Figure 1:
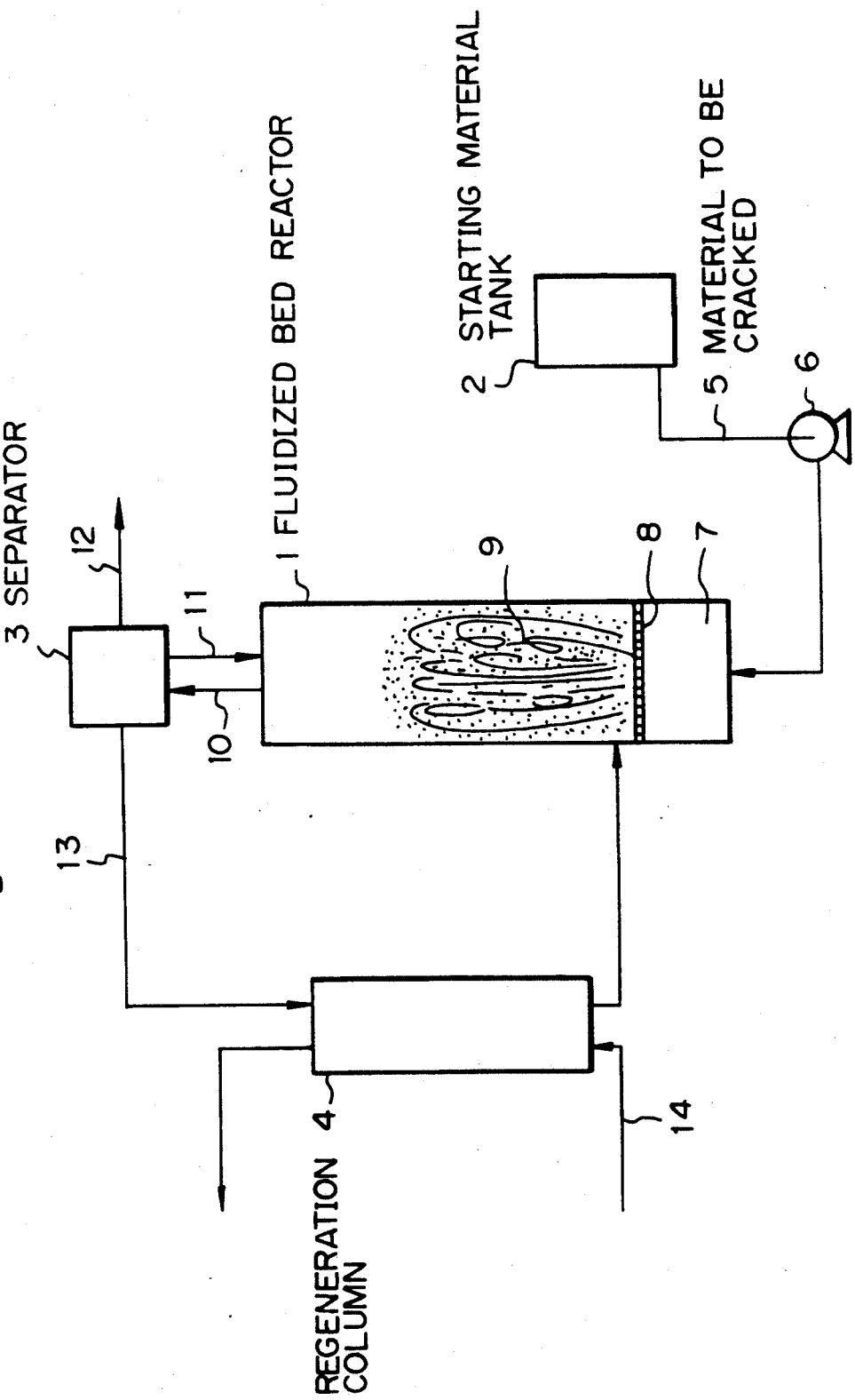
FIG. 1 is a schematic flow diagram process illustrating an example of the fluidized bed type catalytic cracking process, in which reference numeral 1 represents a fluidized bed reactor, reference numeral 2 represents a starting material tank, reference numeral 3 represents a separator, and reference numeral 4 represents a regeneration column.

In principle, the present invention comprises the first reaction of catalytically cracking a hydrocarbon (a) in the presence of a catalytic cracking catalyst to convert the hydrocarbon (a) to a hydrocarbon (b), and the second reaction of dehydrogenating the hydrocarbon (b) obtained by the first reaction to convert the hydrocarbon (b) to a hydrocarbon (c).

Starting Material

The hydrocarbon (a) used as the starting material in the present invention is a paraffin having 5 to 10 carbon atoms as the main component. As specific example of the paraffin, there can be mentioned n-pentane, 2-methylbutane, n-hexane, 3-methylpentane, 2,2-dimethyl-butane, 2,3-dimethylbutane, n-heptane, 2-methylhexane, 3-methylhexane, 3-ethylpentane, 2,2-dimethylpentane, 2,3-dimethylpentane, 2,4-dimethylpentane, 2,2,3-trimethylbutene, n-octane, 3-ethylhexane, 2,5-dimethyl hexane, nonane and decane. Among them, n-hexane, 3-methylpentane, 2,3-dimethylbutane, n-heptane, 2-methyl-hexane, 3-methylhexane, 3-ethylpentane, 2,2-dimethylpentane, 2,3-dimethylpentane and 2,4-dimethylpentane are preferably used in the present invention.

In the first reaction of the present invention, one of the above-mentioned paraffins or a mixture of two or more of them is catalytically cracked in the presence of a catalytic cracking catalyst having a strong acidity. Furthermore, a hydrocarbon mixture comprising the above-mentioned paraffin and other hydrocarbon, for example, an aromatic component, naphthine component or olefin component such as cyclohexane, cyclohexene, benzene, decalin, tetralin, hexene or octene, in which the content of the paraffin having 5 to 10 carbon atoms is at least 30% by weight, especially at least 50% by weight, can be used as the starting material. As the hydrocarbon mixture used as the starting meterial in the present invention, there can be mentioned soft naphtha having a boiling point of 30° to 130° C., which is obtained by distillation separation or catalytic cracking of crude oil.

Catalytic Cracking Reaction

A catalytic cracking catalyst having a strong acidity, which is capable of catalytically cracking the hydrocarbon (a) to convert it to the hydrocarbon (b), is used as the catalytic cracking catalyst at the first reaction. A solid acid catalyst in which the acid quantity at an acid strength function Ho of $< -8.2$ is at least 0.05 millimole/g, especially at least 0.1 millimole/g, is advantageously used as the catalytic cracking catalyst having a strong acidity. The acid strength distribution of the solid acid can be determined by the n-butylamine titration method using a Hammett indicator. The acid quantity at the above-mentioned acid strength distribution can be determined by the titration using n-butylamine as the indicator.

A mordenite catalyst having the above-mentioned acid strength distribution can be mentioned as the solid acid catalyst having the above-mentioned acid strength distribution, though the catalyst used in the present invention is by no means limited to this mordenite catalyst.

In mordenite catalysts, the acid strength increases with increase of the sillica/alumina molar ratio. Furthermore, if mordenites are ion-exchanged with hydrogen, the acid strength increases.

The mordenite is a zeolite having a specific crystal structure called "mordenite structure" and is a tectoalumino-silicate having an ion-exchangeable cation, such as sodium, potassium or calcium, which is naturally produced or is available in the form of a synthetic product.

The mordenite in which the cation is exchanged with a hydrogen ion is a hydrogen ion-exchanged mordenite, and the mordenite in which the cation or hydrogen ion is exchanged with a rare earth metal is a rare earth metal-exchanged mordenite.

In accordance with one preferred embodiment of the present invention, a mordenite ion-exchanged with a rare earth element is used as the catalytic cracking catalyst. Lanthanum and cerium are preferable as the rare earth element. Furthermore, there can be used yttrium, scandium, praseodymium, neodium, promethium, samarium, europium, gadolinium, terbium, dysprosium, holmium, erbium, thulium, ytterbium and lutetium. These rare earths can be used singly or in the form of mixtures of two or more of them. The content of the rare earth metal ion in the catalyst is not particularly critical, but it is generally preferred that the content of the rare earth metal ion be 0.5 to 10% by weight, especially 1 to 5% by weight, based on the catalyst. The ion exchange treatment with the rare earth metal component can be performed by using an aqueous solution of a water-soluble salt, such as a nitrate, of the rare earth element and bringing a mordenite or a hydrogen ion-exchanged mordenite into contact with this aqueous solution.

In accordance with another preferred embodiment of the present invention, a mordenite dealuminized by an acid treatment is used as the catalytic cracking catalyst. This catalyst is a dealuminized mordenite type zeolite catalyst in which a part or majority of aluminum is removed by an acid treatment and the silica/alumina molar ratio is from 12 to 70, preferably from 15 to 60. In the mordenite type zeolite before the dealuminizing treatment, the silica/alumina molar ratio is generally from 10 to 11.

The dealuminized mordenite type zeolite used in the present invention can be prepared by acid-treating the above-mentioned mordenite type zeolite to elute a part or majority of aluminum and then carrying out water washing, drying and firing.

As the acid used at the acid treatment, there can be mentioned mineral acids such as sulfuric acid, hydrochloric acid and nitric acid. The acid is used in an amount of 0.005 to 1 mole, preferable 0.01 to 0.5 mole, per gram of the mordenite type zeolite. The acid is preferably used in the form of an aqueous solution having a concentration of 0.1 N to 10N. In general, the acid treatment temperature is in the range of from room temperature to 90° C. and the acid treatment time is from 0.1 to 30 hours.

After the acid treatment, the dealuminized mordenite type zeolite is sufficiently washed and dried. The drying method is not particularly critical, but it is generally sufficient if the drying is carried out at 80° to 200° C. for 1 to 50 hours.

The dried dealuminized mordenite type zeolite is fired. The firing temperature is ordinarily 300 to 700° C. and preferably 400° to 600° C., and the firing time is generally 0.1 to 10 hours and preferably 1 to 5 hours.

The dealuminized mordenite type zeolite which has been passed through the dealuminizing treatment under the above-mentioned conditions can be directly used as the catalyst.

In the present invention, a hydrogen ion type mordenite in which the silica/alumina molar ratio is in the range of from 10 to 80, especially from 15 to 60, can be used as the mordenite catalyst having a strong acidity.

Furthermore, a solid super-strong acid catalyst can be used. For example, there can be mentioned catalysts prepared by making an $SO_4^{2-}$ ion adsorbed in a carrier composed of $Zr(OH)_4$, $ZrO_2$, $H_4TiO_4$, $TiO_2$ or $Fe_2O_3$. These catalysts can be prepared according to the method customarily adopted for the production of ordinary solid super-strong acid catalysts.

The first reaction of the present invention is a catalytic cracking reaction, and by using the above-mentioned catalytic cracking catalyst having a strong acidity, a paraffin having 5 to 10 carbon atoms or a hydrocarbon comprising this paraffin as the main component as the hydrocarbon (a) is catalytically cracked to form a hydrocarbon (b) comprising a paraffin having 3 or 4 carbon atoms as the main component. A known gas-phase catalytic reaction apparatus can be used for this reaction. For example, a fixed bed type reaction apparatus, a moving bed type reaction apparatus and a fluidized bed type reaction apparatus can be used.

It is preferred that the first reaction of the present invention be carried out at a reaction temperature of 250° to 580° C., especially 300° to 550° C. If the reaction temperature is lower than 250° C., cracking of the starting hydrocarbon (a) is hardly caused and no good results can be obtained. If the reaction is higher than 580° C., formation of hydrocarbon having 1 or 2 carbon atoms, such as methane and ethane, as by-products becomes conspicuous and selectivity to the hydrocarbon (b) comprising a paraffin having 3 or 4 carbon atoms as the main component is reduced, and good results cannot be obtained.

In accordance with a preferred embodiment of the present invention, a fluidized bed type reaction apparatus is used as the reaction apparatus and the catalytic reaction is carried out by the fluidized bed method.

FIG. 1 is a schematic diagram illustrating the fluidized bed type catalytic cracking method, in which reference numeral 1 represents a fluidized bed reactor, reference numeral 2 represents a starting material tank, reference numeral 3 represents a separator and reference numeral 4 represents a regeneration column.

The structure of the fluidized bed type reactor is not particularly critical, so far as the cracking catalyst is fluidized by a fluid comprising the starting material to be cracked and/or the cracking product, but use of a tubular reactor is generally preferable.

The mordenite type zeolite catalyst to be packed in the fluidized bed type reactor 1 can be used singly, or it can be used in the form of a mixture with a metal oxide such as silica/alumina, alumina or other zeolite. The particle size of the cracking catalyst is not particularly critical so far as the fluidized state is stably formed, but it is generally preferred that the average particle size be smaller than 100 μm.

In the fluidized bed type catalytic cracking reaction, a material 5 to be cracked is introduced into the fluidized bed type reactor 1 from the starting material tank 2 by a pump 6, and the starting material 5 is preheated and gasified in a preheating layer 7. The gas is allowed to rise through a partition plate 8 and fluidizes a catalyst layer 9 to form a fluidized bed, whereby the catalytic cracking is effected.

The residence time of the starting material to be cracking depends on the cracked activity of the catalyst, but the residence time is generally 1 to 100 seconds and preferably 5 to 30 seconds.

The cracking reaction can be carried out at a reaction temperature of 250° to 580° C., preferably 300° to 550° C. If the reaction temperature is lower than 250° C., the cracking reaction speed is drastically reduced, and if the reaction temperature is higher than 580° C., coking deterioration is violent and good results cannot be obtained.

A part of the cracking catalyst is withdrawn from the reactor 1 together with a reaction fluid 10 and is separated from the reaction fluid 10 in the separator 3, and a part of the separated catalyst is returned to the reactor 1. A product gas containing a paraffin having 3 or 4 carbon atoms is recovered from the separator 3.

Since the cracking activity of the withdrawn catalyst is reduced by coking, after the separation from the cracking product, a part 13 of the catalyst is introduced into the regeneration column 4 and is regenerated by an ordinary burning regeneration treatment by supplied air 14. The regeneration operation can be carried out in a continuous manner or batchwise. The regenerated catalyst having a completely restored cracking activity is supplied again to the reactor 1 in an amount corresponding to the amount of the withdrawn catalyst. The regenerated catalyst can be supplied to the reactor continuously or intermittently. It is generally preferred that the burning regeneration be carried out at a temperature of 400° to 800° C. If the temperature is lower than 400° C., the regeneration treating speed is extremely low, and if the temperature is higher than 800° C., there is a risk of occurrence of a structural change in the catalyst.

In the catalytic decomposition reaction, the residence time of the reaction mixture is preferably 0.1 to 100 seconds generally, and 0.5 to 20 seconds especially.

The second reaction of the present invention is a dehydrogenation reaction, and the hydrocarbon (b) obtained by the catalytic cracking of the first reaction stage is dehydrogenated by using the dehydrogenation catalyst to convert the paraffin to an olefin, whereby the intended hydrocarbon (c) is prepared from the hydrocarbon (b). An ordinary dehydrogenation catalyst such as a catalyst comprising aluminum oxide and chromium oxide, a catalyst comprising iron oxide and chromium oxide, and noble metal-containing catalysts may be used as the dehydrogenation catalyst in this invention. The noble metal containing catalysts that can be used may be, for example, platinum-containing mordenite, platinum-containing Y-type zeolite, platinum-containing ZSM-5, platinum-containing silica-alumina, platinum-containing aluminum and platinum/palladium-containing mordenite catalysts. A known gas-phase catalytic reaction apparatus can be used for this dehydrogenation reaction. The dehydrogenation reaction temperature is generally 400° to 650° C. and preferably 450° to 600° C. It is preferred that the dehydrogenation reaction be carried out at a temperature higher than the temperature of the first reaction.

The cracking product obtained at the first reaction can be directly used for the second reaction of the present invention. Since the cracking product of the first reaction is obtained in the gas phase, this can be directly supplied to the reaction apparatus of the second stage. If the catalyst used at the first reaction is contained in this gas-phase cracking product, it is preferred that the gas-phase cracking product be supplied to the reaction apparatus of the second stage after the catalyst has been separated. There can be adopted a method in which high-boiling-point fractions contained in the cracking product are separated and only a low-boiling-point component comprising a paraffin having 3 or 4 carbon atoms is supplied.

At the dehydrogenation reaction of the second stage, there can be adopted a method in which the dehydrogenation is carried out while adding an appropriate amount of steam or hydrogen gas to the reaction system.

At the above reaction, the reaction product coming from the reaction apparatus is cooled and separated into a gas product and a liquid product, and each product is separated by rectification or the like.

The reaction product obtained by the first reaction of the present invention is the hydrocarbon comprising a paraffin having 3 or 4 carbon atoms as the main component, which is obtained by cracking the paraffin of the starting hydrocarbon (a) to reduce the carbon number. The reaction product of the above-mentioned catalytic cracking reaction comprises a paraffin having 1 to 5 carbon atoms, such as methane, ethane, propane, butane, isobutane, pentane or isopentane, and an olefin having 2 to 5 carbon atoms, such as ethylene, propylene, 1-butene, 2-butene (cis or trans), isobutene or pentene.

At the second reaction of the present invention, the reaction product obtained by the dehydrogenation reaction is a lower aliphatic hydrocarbon (c) comprising an olefin having 3 or 4 carbon atoms as the main component. The dehydrogenation product contains a paraffin having 1 to 5 carbon atoms, such as methane, ethane, propane, butane, isobutane, pentane or isopentane, and an olefin having 2 to 5 carbon atoms, such as ethylene, propylene, 1-butene, 2-butene (cis or trans), isobutene or pentene, but according to the process of the present invention, an olefin having 3 or 4 carbon atoms can be obtained as the main product among these hydrocarbons.

According to the present invention, as the reaction of preparing a lower aliphatic hydrocarbon (c) comprising an olefin having 3 or 4 carbon atoms as the main component from (a) a paraffin having 5 to 10 carbon atoms or a hydrocarbon comprising this paraffin as the main component, there is adopted a two-staged reaction comprising a first reaction of catalytically cracking the hydrocarbon (a) in the presence of a catalytic cracking catalyst having a strong acidity to convert it to a hydrocarbon (b) comprising a paraffin having 3 or 4 carbon atoms as the main component and a second reaction of dehydrogenating the hydrocarbon (b) obtained by the first reaction by using a dehydrogenation catalyst to convert the hydrocarbon (b) to an olefin hydrocarbon (c). Accordingly, the intended olefin hydrocarbon (c) can be obtained at a high selectivity and in a high yield while controlling formation of hydrocarbons having 1 or 2 carbon atoms.

According to the fluidized bed type preparation process of the present invention, by using a mordenite type zeolite as the catalyst and carrying out the catalytic cracking reaction by the fluidized bed method, propane and butane can be obtained in a high yield. Furthermore, since the catalyst deteriorated by coking can be withdrawn from the reaction system and regenerated by burning without interruption of the cracking reaction, a constant reaction product can be continuously obtained. Therefore, complicated troubles included in the conventional cracking operation can be eliminated, and the separating and purifying steps can be simplified.

The present invention will now be described in detail with reference to the following examples that by no means limit the scope of the invention.

EXAMPLE 1

A Pyrex reaction tube was filled with 5 g of a catalyst (hereinafter referred to as "H-M") composed of a hydrogen ion-exchanged mordenite (TSZ supplied by Toso) having a silica/alumina molar ratio of 15, and the catalyst was heated at 400° C. while supplying nitrogen gas into the reaction tube. When the temperature arrived at the predetermined level, naphtha was supplied at a rate of 10 ml/hr to effect cracking reaction.

After naphtha had been passed through the reaction tube for 2 hours, the obtained cracking product having a composition shown in Table 1 was introduced into a fixed bed reaction apparatus heated at 550° C., which was filled with 10 g of an aluminum oxide/chromium oxide catalyst to effect dehydrogenation reaction. A dehydrogenation product having a composition shown in Table 1 was obtained.

EXAMPLE 2

In 500 ml of distilled water was dissolved 100 g of lanthanum nitrate hexahydrate, and 20 g of H-M used in Example 1 was added to the solution and the ion exchange was carried out at 90° C. for 7 hours. After water washing and drying, firing was carried out at 500° C. for 3 hours to obtain a catalytic cracking catalyst (hereinafter referred to as "La-M"). Lanthanum was contained in an amount of 1.1% by weight in the obtained catalyst.

The cracking reaction and dehydrogenation reaction were carried out in the same manner as described in Example 1 except that the so-obtained catalyst La-M was used as the catalytic cracking catalyst. The obtained results are shown in Table 1.

EXAMPLE 3

In 2 of distilled water was dissolved 200 g of $ZrOCl_2.8H_2O$, and aqueous ammonia was added dropwise with stirring to adjust the pH value of the solution to about 8. The reaction product was washed with water and dried at 100° C. a whole day and night to obtain a hydroxide of zirconium. The hydroxide was pulverized to a size smaller than 2 mesh and 2 g of the pulverized hydroxide was placed on a filter paper, and 30 ml of a 1N aqueous solution of sulfuric acid was poured on the pulverized hydroxide to make $SO_4{}^{2-}$ adsorbed in the pulverized hydroxide. The hydroxide was air-dried and fired at 600° C. in air for 3 hours to obtain a catalytic cracking catalyst (hereinafter referred to as "$SO_4{}^{2-}\cdot ZrO_2$").

The cracking reaction and dehdyrogenation reaction were carried out under the same conditions as described in Example 1 except that this $SO_4{}^{2-}\cdot ZrO_2$ catalyst was used as the catalytic cracking catalyst. The obtained results are shown in Table 1.

EXAMPLE 4

To 300 ml of a 1N aqueous solution of hydrochloric acid was added 20 g of H-M having a silica/alumina molar ratio of 11, and the dealuminizing treatment was carried out at about 80° C. The dealuminized product was washed with water, dried at 100° C. for 5 hours and fired at 500° C. for 3 hours to obtain a catalytic cracking catalyst (hereinafter referred to as "dealuminized M"). The silica/alumina ratio in the obtained catalyst was 24.

The cracking reaction and dehydrogenation reaction were carried out under the same conditions as described in Example 1 except that the obtained dealuminized M catalyst was used as the catalytic cracking catalyst. The obtained results are shown in Table 1.

COMPARATIVE EXAMPLE 1

A liquid mixture (A) comprising 180 g of distilled water, 6.48 g of $Al_2(SO_4)_3 \cdot nH_2O$ (n is 16 to 18), 18.6 g of $H_2SO_4$ (>95%) and 22.6 g of $(CH_3CH_2CH_2)_4NBr$, a liquid mixture (B) comprising 133 g of distilled water and 207 g of water glass No. 3 ($SiO_2=28.9\%$, $Na_2O=9.28\%$) and a liquid mixture (C) comprising 313 g of distilled water and 78.8 g of NaCl were independently prepared.

The liquid mixtures (A) and (B) were charged in dropping funnels, respectively, and they were dropped into the liquid mixture (C) with stirring, while maintaining the pH value of the mixed liquid at 9 to 11. The mixed liquid was placed in an autoclave and reaction was carried out at 160° C. for 20 hours with stirring. The reaction product was washed with water, dried and fired at 530° C. in air for 3 hours to obtain ZSM-5. Then, ZSM-5 was treated with 1N hydrochloric acid to obtain H-ZSM-5.

Then, 20 g of H-ZSM-5 was added to an aqueous solution of $H_2(PtCl_4)$ prepared so that the amount supported of Pt was 1% by weight. The mixture was heated at 60° C. with stirring for 1 hour, and water was removed under heating at 90° C.

The reaction product was fired at 500° C. for 3 hours in air and filled in a Pyrex glass reaction tube. Hydrogen gas was gradually fed under heating at 300° C. and a reduction treatment was carried out for 3 hours to obtain a cracking and dehydrogenation catalyst (hereinafter referred to as "Pt/ZSM-5").

A quartz reaction tube was packed with 10 g of Pt/ZSM-5 and heated at 550° C., and light naphtha was fed at a rate of 5 ml/hr to effect reaction. The obtained results are shown in Table 1.

EXAMPLES 5 AND 6

Example 1 was repeated except that the dehydrogenation catalyst was changed to 1% $Pt/SiO_2.Al_2O_3$ (Example 5) or 1% Pt/mordenite-type zeolite (Example 6). The results are shown in Table 1.

TABLE 1

|  | Example 1 | Example 2 | Example 3 | Example 4 | Comparative Example 1 | Example 5 | Example 6 |
|---|---|---|---|---|---|---|---|
| Catalytic Cracking Catalyst | H—M | La—M | $SO_4{}^{2-}.ZrO_2$ | dealuminized | Pt/ZSM-5 | H—M | H—M |
| Dehydrogenation Catalyst | $Al_2O_3.Cr_2O_3$ | $Al_2O_3.Cr_2O_3$ | $Al_2O_3.Cr_2O_3$ | $Al_2O_3.Cr_2O_3$ |  | 1% Pt/ $SiO_2.Al_2O_3$ | 1% Pt/ moldenite |
| Composition of Cracking Product (% by weight) |  |  |  |  |  |  |  |
| methane, ethane, ethylene | 1 | 2 | 1 | 2 | — | 1 | 1 |
| propane, butane | 65 | 73 | 54 | 78 | — | 65 | 65 |
| propylene, butene | 1 | 2 | 0 | 1 | — | 1 | 1 |
| others | 33 | 23 | 45 | 19 | — | 33 | 33 |
| Composition of Dehydrogenation Product (% by weight) |  |  |  |  |  |  |  |
| methane, ethane, ethylene | 6 | 8 | 5 | 4 | 33 | 4 | 5 |
| propane, butane | 21 | 25 | 20 | 24 | 10 | 20 | 24 |
| propylene, butene | 40 | 44 | 38 | 53 | 28 | 47 | 56 |
| others | 33 | 23 | 37 | 19 | 19 | 29 | 15 |

EXAMPLE 7-A

In 500 cc of distilled water was dissolved 100 g of lanthanum nitrate hexahydrate, and 20 g of a hydrogen ion type mordenite (TSZ-620 HOA supplied by Toso) was added to the solution, and ion exchange was carried out for 7 hours at 90° C. with stirring. The ion-exchanged mordenite was washed with water, dried and fired at 500° C. for 3 hours to obtain a catalyst. Lanthanum was contained in an amount of 1.1% by weight in the obtained catalyst.

Then, 0.1 g of the obtained catalyst was packed in a pulse reactor connected directly to a gas chromatograph, and light naphtha having a boiling point of 30° to 110° C. under atmosphere pressure was supplied in an amount of 0.5 μl at a reaction temperature of 300° C. to effect cracking reaction. The reaction results are shown in Table 2.

EXAMPLE 7-B

The reaction was carried out under the same conditions as described in Example 7-A except that the hydrogen ion type mordenite was used as the catalyst. The obtained results are shown in Table 2.

EXAMPLES 7-C AND 7-D

The reaction was carried out under the same conditions as described in Example 7-A except that the reaction temperature was changed to 400° C. (Example 7-C)

or 500° C. (Example 7-D) from 300° C. The obtained results are shown in Table 2.

EXAMPLE 7-E

A catalyst was prepared in the same manner as described in Example 7-A except that cerium nitrate hexahydrate was used instead of lanthanum nitrate hexahydrate, and the reaction was carried out under the same conditions as described in Example 7-A by using the obtained catalyst. The obtained results are shown in Table 2. Cerium was contained in an amount of 2.9% by weight in the catalyst.

EXAMPLE 7-F

A catalyst was prepared in the same manner as described in Example 7-A except that the ion exchange was carried out by using a mixture of 100 g of lanthanum nitrate hexahydrate and 100 g of cerium nitrate hexahydrate, and the reaction was carried out under the same conditions as described in Example 7-A by using the obtained catalyst. The obtained results are shown in Table 2. Lanthanum and cerium were contained in amounts of 0.5% by weight and 1.6% by weight, respectively.

EXAMPLE 7-G

A micro-reactor was packed with 2 g of the catalyst of Example 7-A, and the continuous reaction was carried out under conditions of a temperature of 400° C. and LHSV of 0.1 hr$^{-1}$. The results obtained when the reaction was conducted for 30 minutes are shown in Table 2.

EXAMPLE 7-H

A catalyst was prepared in the same manner as described in Example 7-A except that a sodium ion type mordenite (620NAA supplied by Toso) was used instead of the hydrogen ion type mordenite and the ion exchange operation was repeated four times. Lanthanum was contained in an amount of 7.8% by weight in the catalyst. Cracking reaction of light naphtha was carried out at 400° C. by using a pulse reactor. The obtained results are shown in Table 2.

EXAMPLE 7-I

The reactor product gas obtained in Example 7-G was introduced in a fixed bed reactor packed with 10 g of an aluminum oxide/chromium oxide catalyst and heated at 550° C. to effect dehydrogenation reaction. The obtained results are shown in Table 2.

TABLE 2

| | Example 7-A | Example 7-B | Example 7-C | Example 7-D | Example 7-E | Example 7-F | Example 7-G | Example 7-H | Example 7-I |
|---|---|---|---|---|---|---|---|---|---|
| Catalyst | La ion-containing mordenite | hydrogen ion type mordenite | La ion-containing mordenite | La ion-containing mordenite | Ce ion-containing mordenite | La, Ce ion-containing mordenite | La ion-containing mordenite | La ion-containing mordenite | La ion-containing zeolite/aluminum oxide, chromium oxide |
| Reaction Temperature (°C.) | 300 | 300 | 400 | 500 | 300 | 300 | 400 | 400 | 400–550 |
| Product Distribution (% by weight) | | | | | | | | | |
| $C_1$, $C_2$ fractions* | 2 | 1 | 2 | 7 | 1 | 1 | 1 | 1 | 4 |
| propane | 32 | 10 | 48 | 70 | 30 | 27 | 20 | 35 | 4 |
| propylene | 1 | 0 | 1 | 2 | 1 | 0 | 0 | 1 | 15 |
| butanes | 48 | 40 | 35 | 11 | 50 | 44 | 38 | 30 | 5 |
| butenes | 1 | 0 | 1 | 1 | 0 | 0 | 0 | 0 | 32 |
| others | 16 | 49 | 13 | 9 | 18 | 28 | 41 | 33 | 40 |

Note
*sum of methane, ethane and ethylene

EXAMPLE 8-A

To 300 ml of a 1N aqueous solution of hydrochloric acid was added 20 g of a hydrogen ion-exchanged mordenite zeolite (hereinafter referred to as "HM") having a silica/alumina molar ratio of 1.0, and a treatment was carried out at about 80° C. for 3 hours. The treated mordenite type zeolite was washed with water, dried at 100° C. for 5 hours and fired at 500° C. for hours to obtain a catalyst. The silica/alumina molar ratio was 24 in the obtained catalyst.

Then, 0.1 g of the obtained catalyst was packed in a pulse reactor connected directly to a gas chromatograph, and 0.5 μl of light naphtha having a boiling point of 30° to 110° C. under atmospheric pressure was fed into the reactor at a reaction temperature of 400° C. to effect cracking reaction. The obtained results are shown in Table 3.

EXAMPLE 8-B

The cracking reaction was carried out under the same conditions as described in Example 1 except that HM before the acid treatment, which had a silica/alumina molar ratio of 10, was used as the catalyst. The obtained results are shown in Table 3.

EXAMPLES 8-C AND 8-D

A catalyst was prepared in the same manner as described in Example 8-A except that hydrochloric acid was changed to sulfuric acid (Example 8-C) or nitric acid (Example 8-D), and the cracking catalyst was carried out under the same conditions as described in Example 8-A except that the obtained catalyst was used. The silica/alumina molar ratio in the catalyst was 16 (Example 8-C) or 20 (Example 8-D). The obtained results are shown in Table 3.

EXAMPLE 8-E

A catalyst was prepared in the same manner as described in Example 8-D except that the acid treatment time was changed to 8 hours. The silica/alumina molar ratio was 30 in the obtained catalyst. The obtained results are shown in Table 3.

EXAMPLE 8-F

The catalytic reaction was carried out under the same conditions as described in Example 8-D except that the catalytic reaction temperature was changed to 300° C. The obtained results are shown in Table 3.

EXAMPLE 8-G

A catalyst was prepared in the same manner as described in Example 8-A except that the acid treatment temperature was changed to 50° C. and the acid treatment time was changed to 10 hours, and the catalytic reaction was carried out under the same conditions as described in Example 8-A except that the obtained catalyst was used. The silica/alumina molar ratio was 19 in the obtained catalyst. The obtained results are shown in Table 3.

TABLE 3

|  | Example 8-A | Example 8-B | Example 8-C | Example 8-D | Example 8-E | Example 8-F | Example 8-G |
|---|---|---|---|---|---|---|---|
| Catalyst | acid-treated HM[2] | un-treated HM | acid-treated HM | acid-treated HM | acid-treated HM | acid-treated HM | acid-treated HM |
| Acid Used for Acid Treatment | hydrochloric acid | — | sulfuric acid | nitric acid | nitric acid | nitric acid | hydrochloric acid |
| Silica/Alumina Molar Ratio in HM | 24 | 10 | 16 | 20 | 30 | 20 | 19 |
| Reaction Temperature (°C.) | 400 | 400 | 400 | 400 | 400 | 300 | 400 |
| Product Distribution (% by weight) | | | | | | | |
| $C_1$, $C_2$ fractions[1] | 2 | 1 | 1 | 2 | 1 | 0 | 2 |
| Propane | 60 | 30 | 52 | 63 | 60 | 24 | 55 |
| Propylene | 1 | 1 | 1 | 1 | 1 | 0 | 1 |
| butanes | 15 | 23 | 12 | 16 | 18 | 45 | 16 |
| butenes | 1 | 1 | 1 | 1 | 1 | 0 | 0 |
| others | 21 | 44 | 33 | 17 | 19 | 31 | 26 |

Note
[1] sum of methane, ethane and ethylene
[2] hydrogen ion-exchanged mordenite type zeolite

EXAMPLE 9-A

A Pyrex reaction tube provided with a partition plate was charged with 5 g of a hydrogen ion-exchanged mordenite (TSZ-620HOA supplied by Toso; particle size =60μm), and the mordenite was heated at 400° C. while feeding nitrogen gas from below the partition plate. After the temperature arrived at the predetermined level, light naphtha (liquid fraction having a boiling point of 30° to 110° C. under atmospheric pressure) was fed at a rate of 10 ml/hr from the lower portion of the reaction tube. The naphtha was gasified in a preheating layer and the starting fluid to be cracked was fed into the catalyst layer from below the partition plate to fluidize the catalyst and effect cracking reaction. This cracking reaction was continuously carried out while feeding the regenerated catalyst to the reaction in an amount corresponding to the amount of the catalyst withdrawn together with the product gas fluid.

The burning regeneration of the catalyst was carried out at 550° C. The cracking reaction results are shown in Table 4.

EXAMPLES 9-B AND 9-C

The cracking reaction was carried out in the same manner as described in Example 9-A except that the catalyst was changed to a hydrogen ion-exchanged mordenite containing 1.0% by weight of a lanthanum ion (Example 9-B) or a hydrogen ion-exchanged mordenite containing 2.5% by weight of a cerium ion (Example 9-C). The cracking reaction results are shown in Table 4.

EXAMPLE 9-D

A Pyrex reaction tube was packed with 5 g of a hydrogen ion-exchanged mordenite, and the mordenite was heated at 400° C. while feeding nitrogen gas. When the temperature arrived at the predetermined level, light naphtha was fed at a rate of 10 ml/hr from the upper portion of the reaction tube to effect cracking reaction. Every time the starting material was supplied for 2 hours, the catalyst was regenerated by carrying out the burning regeneration treatment at 550° C., and the reaction was continued. The obtained results are shown in Table 4.

TABLE 4

| Time (hours) of Supply of Starting Material | Yield (% by weight) of Propane and Butanes | | | |
|---|---|---|---|---|
|  | Example 9-A | Example 9-B | Example 9-C | Example 9-D |
| 0.5 | 42 | 63 | 60 | 31 |
| 1 | 43 | 61 | 58 | 17 |
| 2 | 41 | 64 | 59 | 8 (regeneration treatment) |
| 3 | 44 | 62 | 61 | 30 |
| 4 | 42 | 62 | 62 | 9 (regeneration |

TABLE 4-continued

| Time (hours) of Supply of Starting Material | Yield (% by weight) of Propane and Butanes | | | |
|---|---|---|---|---|
| | Example 9-A | Example 9-B | Example 9-C | Example 9-D |
| | | | | treatment) |
| 5 | 40 | 63 | 61 | 31 |

EXAMPLE 10

A starting material to be dehydrogenated, which was composed of the reaction product gas obtained in Example 9-B when the starting material was supplied for 3 hours and which had a composition shown in Table 5 was introduced into a fixed bed reactor packed with 10 g of an aluminum oxide/chromium oxide catalyst and heated at 550° C. to effect dehydrogenation reaction. A dehydrogenation product having a composition shown in Table 5 was obtained.

TABLE 5

| | methane, ethane, ethylene | propane, butanes | propylene, butenes |
|---|---|---|---|
| starting material to be dehydrogenated | 1 | 62 | 0 |
| dehydrogenation product | 5 | 15 | 41 |

We claim:

1. A process for the preparation of a lower aliphatic hydrocarbon comprising at least 30% by weight of an olefin having 3 to 4 carbon atoms from a first paraffin having 5 to 10 carbon atoms or a first hydrocarbon comprising at least 30% by weight of said first paraffin, which comprises:
   carrying out a first reaction of catalytically cracking said first paraffin having 5 to 10 carbon atoms or said first hydrocarbon comprising at least 30% by weight of said first paraffin in the presence of a catalytic cracking catalyst having a strong acidity selected from the group consisting of
   a mordenite catalyst dealuminized by an acid treatment to produce a silica/alumina molar ratio of from 12 to 70, and a solid super-strong acid catalyst formed by supporting a sulfuric acid ion on a carrier composed of $Zr(OH)_4$, $ZrO_2$, $H_4TiO_4$, $TiO_2$ or $Fe_2O_3$,
   to convert said first paraffin or said first hydrocarbon to a second hydrocarbon comprising at least 30% by weight of a second paraffin having 3 to 3 carbon atoms; and
   carrying out a second reaction of dehydrogenating said second hydrocarbon comprising at least 30% by weight of said second paraffin having 3 to 4 carbon atoms obtained in said first reaction with a dehydrogenation catalyst to convert said second hydrocarbon to a lower aliphatic hydrocarbon comprising at least 30% by weight of an olefin having 3 to 4 carbon atoms.

2. A process according to claim 1, wherein the catalytic cracking catalyst is a mordenite containing a rare earth metal component introduced by ion exchange.

3. A process according to claim 2, wherein the rare earth metal component is contained in an amount of 0.1 to 10% by weight as the oxide.

4. A process according to claim 2, wherein the rare earth metal component is lanthanum or cerium.

5. A process according to claim 1, wherein the dealuminized mordenite catalyst is one prepared by treating a mordenite with an acid in an amount of 0.005 to 1 mole per gram of the mordenite, drying the acid-treated mordenite and firing the dried acid-treated mordenite at a temperature of 300° to 700° C.

6. A process according to claim 1, wherein the dehydrogenation catalyst is an aluminum oxide/chromium oxide catalyst, an iron oxide/chromium oxide catalyst or a noble metal-containing catalyst.

7. A process according to claim 1, wherein the catalytic cracking reaction is carried out at a temperature of 250° to 580° C. and the dehydrogenation reaction is carried out at a temperature of 450° to 600° C.

8. A process according to claim 1, wherein the catalytic cracking reaction is effected by contacting said first hydrocarbon with the catalytic cracking catalyst in a fluidized bed.

9. A process for the preparation of a lower aliphatic hydrocarbon, according to claim 2, wherein the rare earth metal component comprises 1 to 5% by weight, based on the weight of the catalyst.

10. A process for the preparation of a lower aliphatic hydrocarbon according to claim 9, wherein the rare earth element is lanthanum or cerium.

11. A process according to claim 1, wherein the dealuminized mordenite catalyst is fired at a temperature of 400° to 600° for 1 to 5 hours.

12. A process for the preparation of a lower aliphatic hydrocarbon, which comprises catalytically cracking a paraffin having 5 to 10 carbon atoms or a hydrocarbon comprising at least 30% by weight of said paraffin to form a lower aliphatic hydrocarbon comprising at least 30% by weight of a paraffin having 3 to 4 carbon atoms in the presence of a mordenite catalyst dealuminized by an acid treatment to produce a silica/alumina molar ratio of from 12 to 70.

13. A process according to claim 8, wherein the catalytic cracking reaction is effected by contacting the starting hydrocarbon with the catalytic cracking catalyst in a fluidized bed.

14. A process for the preparation of a lower aliphatic hydrocarbon comprising at least 30% by weight of a paraffin having 3 to 4 carbon atoms which comprises:
   bringing a paraffin having 5 to 10 carbon atoms or a hydrocarbon comprising at least 30% by weight of said paraffin into contact with a catalyst composed of a mordenite, dealuminized by an acid treatment to produce a silica/alumina molar ratio of from 12 to 70, at a temperature of 300° to 550° C. in a fluidized bed to form a cracking reaction product comprising at least 30% by weight of a paraffin having 3 or 4 carbon atoms;
   withdrawing a part of the catalyst together with the cracking product from the fluidized bed;
   separating the cracking catalyst from the cracking reaction product;
   regenerating the separated catalyst by a burning treatment at a temperature of 400° to 800° C.; and circulating the regenerated catalyst to the fluidized bed.

15. A process for the preparation of a lower alphatic hydrocarbon, which comprises catalytically cracking a paraffin having 5 to 10 carbon atoms or a hydrocarbon comprising at least 30% by weight of said paraffin to form a lower aliphatic hydrocarbon comprising at least 30% by weight of a paraffin having 3 to 4 carbon atoms in the presence of a solid super-strong acid catalyst which is formed by supporting a sulfuric acid ion on a carrier compounds of $Zr(OH)_4$, $ZrO_2$, $H_4TiO_4$, $TiO_2$ or $Fe_2O_3$.

* * * * *